United States Patent
Speier (10) Patent No.: US 9,188,559 B2
(45) Date of Patent: Nov. 17, 2015

(54) TEST METHOD AND TESTING DEVICE FOR NOZZLES AND NOZZLE

(75) Inventor: Juergen Speier, Reutlingen (DE)

(73) Assignee: LECHLER GMBH, Metzingen (DE)

( * ) Notice: Subject to any disclaimer, the term of this patent is extended or adjusted under 35 U.S.C. 154(b) by 491 days.

(21) Appl. No.: 13/438,992

(22) Filed: Apr. 4, 2012

(65) Prior Publication Data

US 2012/0263208 A1 Oct. 18, 2012

(30) Foreign Application Priority Data

Apr. 12, 2011 (DE) .................. 10 2011 007 230

(51) Int. Cl.
*G01N 25/72* (2006.01)

(52) U.S. Cl.
CPC ........................... *G01N 25/72* (2013.01)

(58) Field of Classification Search
CPC ...................................................... G01N 25/72
USPC ............................... 73/606; 250/341.6; 374/5
See application file for complete search history.

(56) References Cited

U.S. PATENT DOCUMENTS

| 4,988,210 | A  * | 1/1991 | Koshihara et al. ................. 374/5 |
| 6,838,670 | B2 * | 1/2005 | Lewis et al. ................. 250/341.6 |
| 2003/0010124 | A1 | 1/2003 | Bates |
| 2012/0062751 | A1 | 3/2012 | Homma et al. |

FOREIGN PATENT DOCUMENTS

| AT | 505 813 B1 | 6/2009 |
| DE | 100 59 854 A1 | 6/2002 |
| DE | 101 44 408 A1 | 4/2003 |
| DE | 10 2007 043 364 A1 | 4/2009 |
| DE | 10 2009 021 233 A1 | 11/2010 |
| EP | 1 898 213 A1 | 3/2008 |
| WO | WO 2004/020993 A2 | 3/2004 |

* cited by examiner

*Primary Examiner* — John Chapman, Jr.
(74) *Attorney, Agent, or Firm* — Flynn, Thiel, Boutell & Tanis, P.C.

(57) ABSTRACT

The invention relates to a test method for nozzles composed of ceramic or ceramic-like materials, in which the following method steps are carried out: transfer of ultrasonic vibration to the nozzle by means of a sonotrode placed against the nozzle and thermographic evaluation of the heat evolved in a wall of the nozzle.

26 Claims, 5 Drawing Sheets

TEST METHOD AND TESTING DEVICE FOR NOZZLES AND NOZZLE

CROSS REFERENCE TO RELATED APPLICATION

This application claims the priority of German Application No. 10 2011 007 230.6, filed Apr. 12, 2011, the disclosure of which is hereby incorporated by reference in its entirety into this application.

FIELD OF THE INVENTION

The invention relates to a test method for nozzles composed of ceramic or ceramic-like materials. The invention also relates to a testing device for nozzles composed of ceramic or ceramic-like materials. Finally, the invention relates to a nozzle that is composed of ceramic or ceramic-like material and that has at least one wall.

BACKGROUND OF THE INVENTION

The German unexamined laid-open patent application DE 100 59 854 A1 discloses a thermographic test method in which a specimen surface is excited by the transfer of ultrasound thereto and then evaluated by means of a thermal imaging camera. When ultrasound is transferred to a defective component, the ultrasonic energy is preferentially converted to heat at the defective locations.

Finding cracks in ceramic nozzles has been found to be problematic in the prior art. Usually, an experienced quality assurance representative uses a small hammer to tap on ceramic nozzles, which always comprise at least one cavity. The sound resulting when the nozzles are tapped on then serves as an indication of cracks and/or defects that may exist in the nozzles. The examination of ceramic nozzles by means of automated, mechanical processes poses great problems, since nozzles composed of ceramic or ceramic-like materials are fragile under conditions of exposure to severe mechanical and/or thermal stresses.

SUMMARY OF THE INVENTION

It is an object of the invention to improve a test method, a testing device, and a nozzle composed of ceramic or ceramic-like material.

According to the invention, there is provided, to this end, a test method for nozzles composed of ceramic or ceramic-like materials, which includes the following steps: the transfer of ultrasonic vibration to the nozzle, more particularly by means of a sonotrode placed against the nozzle, and the thermographic evaluation of the heat evolved in a wall of the nozzle.

The thermographic evaluation is then carried out during or after the transfer of ultrasonic vibration by means of an ultrasonic transducer or a sonotrode, or alternatively by means of a loudspeaker, for example. A greater amount of heat is evolved in cracks or defects in the wall of the nozzle, and this heat can then be detected by thermographic evaluation. When ultrasonic vibration is transferred to the nozzle, it has been found, surprisingly, that cracks and defects in the ceramic material are detected effectively and that only those nozzles that are already severely damaged break to pieces as a result of the transfer of ultrasonic energy under test conditions. Thus the test method of the invention makes it possible to detect cracks and defects in nozzles that are composed of ceramic or ceramic-like materials and that comprise at least one cavity and then to assess the detected cracks or defects in order to decide whether these nozzles can be used and, if so, for which application they would be suitable. The transfer of ultrasonic vibration and the thermographic evaluation allow the examination of nozzles to be carried out without having to depend on the experience of a crack detector and also the detection of cracks or defects that are small or hidden from view and do not extend directly to the surface of the nozzle. Such small defects in critical, highly stressed regions of the nozzle can then lead to malfunction of the nozzle during continuous operation. The test method of the invention remedies such a situation and enables the tested nozzles to be provided with a long service life warranty. Nozzles composed of ceramic or ceramic-like materials comprise at least one cavity. The term "cavity" is understood to mean an enclosed space comprising one or more orifices, for example, a swirl chamber or a through-flow passage in a solid stream nozzle comprising an inlet orifice and an outlet orifice. Nozzles composed of ceramic or ceramic-like materials are always fragile on account of the cavity, and the examination of such nozzles always poses problems, since such examination must include an inspection of all the walls of the cavity and also of all additional, fragile components of the nozzle. The invention provides a surprisingly simple remedy for nozzles comprising at least one cavity.

In a development of the invention, the sonotrode is placed against a connecting region or a chamber region of the nozzle.

Nozzles composed of ceramic or ceramic-like materials generally consist of a connecting region and at least one chamber region, and an inlet region, by means of which the liquid to be sprayed is conveyed from the connecting region to the chamber region. The connecting region can be composed of, for example, a flange, a circular screw thread, a connecting component for gluing, or the like. The inlet is usually of a tubular shape. The chamber region can comprise, for example, one or more swirl chambers. The most important region to be examined is the inlet region, since this must absorb the greatest stresses not only during the operation of the nozzle but also during fabrication thereof. Therefore, it is not possible to simulate satisfactorily, if at all, the stresses applied to the nozzles during operation by positioning the sonotrode in the inlet region. Rather, the sonotrode is positioned on one of the two portions of greater mass, namely the connecting region or the chamber region, so that oscillation of maximum possible amplitude is induced in the other portion of greater mass, that is to say, in the chamber region or the connecting region, respectively. This then allows the critical inlet region to be tested effectively by means of the test method of the invention. According to the invention, it is preferred to position the sonotrode in the connecting region, since such an approach corresponds most closely to the actual operating conditions. During actual operation, a nozzle is mounted by means of its connecting region on a connecting pipe and vibration caused, for example, by pumps or the fluid flow in the connecting pipe, is transferred from the connecting pipe to the swirl chamber of the nozzle by way of the inlet.

In a development of the invention, the sonotrode is placed against the peripheral surface of a connecting component, more specifically a connecting flange.

In this way, ultrasonic vibration can be transferred to the nozzle reliably and without much risk of damage to the nozzle.

In a development of the invention, the sonotrode is placed against a flat surface in the connecting region or in the chamber region of the nozzle.

Contact over a flat area between the sonotrode and the ceramic component with interposition of an intermediate component, if appropriate, is preferable for the input of ultrasonic energy because the transfer thereof via point contact can result in damage to both the sonotrode and the nozzle. This can be prevented by providing the nozzle with surfaces showing maximum flatness and having a size that is slightly larger than that of the contact surface of the sonotrode. Advantageously, such a flat surface can be provided in the connecting region or the chamber region of the nozzle in order to achieve a significant examination of the nozzle.

In a development of the invention, the sonotrode is placed against an external or internal surface of a wall in the chamber region of the nozzle.

Apart from the transfer of ultrasound via an external surface of the wall of the nozzle, it is also possible to input ultrasonic energy through an internal surface of a wall in the chamber region of the nozzle.

In a development of the invention, provision is made for the placement of a counterbrace, at a location opposite to the sonotrode, against the internal or external surface of the wall, as appropriate.

A particularly effective transfer of ultrasonic energy can be achieved by the provision of a counterbrace, which is then positioned in the chamber region, for example, against the internal surface of the chamber wall at a location opposite to the sonotrode. For example, such a counterbrace can be inserted to the swirl chamber through an outlet orifice of the nozzle.

In a development of the invention, provision is made for pressing the sonotrode against the nozzle during the transfer of ultrasonic vibration, while at least one counterbrace is provided to counteract the pressing force.

Pressing the sonotrode against the nozzle during the transfer of ultrasonic energy can ensure a particularly effective input of energy.

In a development of the invention, the counterbrace is positioned at two points of contact on the nozzle.

In this way, there is formed, together with the sonotrode, a three-point support for the nozzle. Such a three-point support firstly allows the nozzle to be mounted securely in the testing device and secondly it provides only slight obstruction by the points of contact themselves to the vibration being transferred to the nozzle.

In a development of the invention, a point of contact of the sonotrode and the two points of contact of the counterbrace are located at the corners of a symmetrical planar triangle.

In this way, it is possible to provide more efficient support of the nozzle in the testing device and, apart from the fact that the nozzle is clamped securely, vibration can propagate to the nozzle in order to achieve reliable test results. The ultrasonic energy must be distributed as uniformly as possible over the wall of the nozzle in order to avoid erroneous measurements. If, for example, the ultrasonic energy were to be concentrated in certain regions of the nozzle following the commencement of the transfer of ultrasonic energy, then said regions will be expected to heat up, even if they contain no defects or cracks or only very small defects or cracks, to a greater extent than other regions in which there is less ultrasonic energy present. The arrangement of the points of contact of the sonotrode and the counterbrace as proposed by the invention is conducive to the prevention of such erroneous measurements or false conclusions.

In a development of the invention, there is provided a resilient intermediate component between the sonotrode and the nozzle.

On the one hand, the use of a resilient intermediate component can prevent the ceramic material of the nozzle from being damaged by the sonotrode, and energy can be transferred with only slight loss of ultrasonic energy. On the other hand, a resilient intermediate component can also be used for achieving a match between a contact surface of the sonotrode and an external surface of the nozzle. If, for example, there is no suitable flat surface on the nozzle itself, against which the sonotrode could be placed, it is possible to provide an intermediate component at this location to achieve a match between the mutually opposing surfaces.

Advantageously, the intermediate component has a modulus of elasticity that ranges from 9,000 N/mm$^2$ to 19,000 N/mm$^2$ and is more particularly 14,000 N/mm$^2$.

Such elasticity values have proven to be advantageous in order to achieve an effective excitation of the nozzle at an acceptable loss of ultrasonic energy. For example, hardwood, more particularly beechwood, and also temperature-resistant high performance plastics materials are well-suited for use as an intermediate component. Advantageously, the intermediate component is inserted with its direction of grain extending longitudinally between the sonotrode and the nozzle.

Advantageously, the intermediate component has a thermal conductivity ranging from 0.1 W/mK to 0.2 W/mK.

During the transfer of ultrasonic energy, a considerable amount of heat also evolves in the intermediate component and this heat must be removed appropriately in order to prevent destruction of the intermediate component. A suitable relationship between the modulus of elasticity and the thermal conductivity is also conducive to a longer undisturbed test period during the operation of transferring ultrasonic energy. Intermediate components composed of hardwood, more particularly beechwood, have proven to be advantageous for this purpose. For example, it has been found that PVC-plastics, PE-plastics or folded writing paper likewise enable ultrasonic energy to be transferred to the nozzle, but these materials become so hot after a short period that they are destroyed.

In a development of the invention, provision is made for at least one mirror capable of reflecting thermal radiation to be positioned in the region of the nozzle and for a thermographic evaluation of a mirror image of the nozzle to be carried out.

In this way, it is possible to evaluate the rear side of the nozzle which is remote from the thermal imaging camera without it being necessary to move the camera itself or to use two cameras. In this way, the test method can be carried out economically, on the one hand, and very rapidly, on the other. This feature is of considerable advantage for the series production of nozzles.

In a development of the invention, there is provided a curved or bent mirror.

In this way, it is possible to examine regions of the nozzle that are hidden from view, or for example the complete external wall of the nozzle, by means of a single thermal imaging camera, without having to move this camera or the mirrors. For example, spherical shell-shaped mirrors, parabolic mirrors or bent mirrors having a plurality of flat surfaces inclined at an angle in relation to each other can be used. A distortion of the mirror image of the nozzle as a result of the use of such curved or bent mirrors can either be accepted or, for example, back calculated during the course of the thermographic evaluation.

In a development of the invention, provision is made for the mirror and/or a thermal imaging camera to be moved during the thermographic evaluation.

Movement of the mirror or of the camera optionally combined with the provision of bent or curved mirrors can be useful, for example, to make it possible to carry out a particularly accurate examination of nozzles or an overall examination of nozzles having very complicated geometries.

In a development of the invention, the ultrasonic vibration is transferred at a frequency in the range of 20 kHz.

At such a frequency, it is possible to carry out a reliable examination of the nozzles without increased risk of damage to the nozzles during the test.

In a development of the invention, the transfer of ultrasonic vibration is carried out at a power level which ranges from 100 W to 200 W and is more particularly 150 W.

The transfer of power in the range of from 100 W to 200 W has proven to be sufficient for reliable detection of defects in the ceramic material of the nozzles. At the same time, there is a risk of damage to the nozzles only in the case of nozzles that exhibit severe previous impairment. Thus an acoustic generator having a power level of 500 W is sufficient for carrying out the method of the invention.

In a development of the invention, a mark is provided on the nozzle prior to the thermographic evaluation using a heat-reflecting coating or by marking the nozzle by means of a heat source.

When thermal images are captured by the camera, conventional labels or marks on the nozzle are not visible in the image. By contrast, the use of marks on the nozzle provided by a heat-reflecting coating material, for example, by means of a silver paint stick or a pencil or by marking the nozzle by means of a heat source, for example a laser pointer, can render the mark visible in the thermal image and substantially facilitates the evaluation or archiving of the test findings.

The object of the invention is also achieved by a testing device for nozzles that are composed of ceramic or ceramic-like materials and that comprise at least one cavity, for carrying out the method of the invention, in which testing device there is provided at least one sonotrode for transferring ultrasonic vibration to the nozzle and at least one thermal imaging camera for the thermographic evaluation of the heat evolved in a wall of the cavity of the nozzle.

Advantageously, the testing device comprises heat-reflecting mirrors, and a mirror image of the nozzle is evaluated by means of the thermal imaging camera.

In a development of the invention, provision is made for at least one counterbrace to be placed against the nozzle at a location opposite to the sonotrode.

In a development of the invention, the counterbrace rests against the nozzle at two points of contact that form, together with a point of contact of the sonotrode, a symmetrical planar triangle.

For example, the counterbrace comprises an approximately V-shaped cutout, and a circular annular connecting flange of the nozzle is accommodated in the V-shaped cutout such that it rests against the counterbrace at two opposing points. A sonotrode is then placed against the periphery of the connecting flange at a location opposite to the counterbrace such that the points of contact form a symmetrical triangle.

In a development of the invention, a disk composed of resilient material and having a modulus of elasticity that ranges from 9,000 N/mm$^2$ to 19,000 N/mm$^2$ and is more particularly 14,000 N/mm$^2$ is provided between the sonotrode and the nozzle.

For example, a hardwood disk, more particularly a beechwood disk, can be provided. Advantageously, the wood grain then extends longitudinally between the sonotrode and the nozzle. Disks composed of resilient material, more specifically, wooden disks, having a thickness ranging from 2 mm to 10 mm have proven to be advantageous. It is also possible to use temperature-resistant high performance plastics materials.

The object of the invention is also achieved by a nozzle that is composed of ceramic or ceramic-like material and that comprises at least one cavity and at least one wall delimiting the cavity, in which nozzle the wall has at least a first flat surface, against which a sonotrode can be placed.

In this way, ultrasonic energy can be transferred very effectively to the nozzle by way of the first flat surface. Thus the nozzle of the invention is particularly advantageous, since it can be examined for cracks and defects economically and rapidly.

In a development of the invention, the wall has at least a second flat surface, against which a counterbrace can be placed.

In a development of the invention, the first surface is disposed on an external or internal surface of the wall and the second surface is disposed at a location opposite to the first surface on an internal or external surface of the wall, respectively. In this way, the sonotrode and the counterbrace can be positioned on the nozzle in a simple manner and an effective transfer of ultrasonic energy to the nozzle can occur during the examination of the nozzles. For example, the first flat surface can be disposed on the external surface of a swirl chamber and the second flat surface can be disposed at a location opposite to the first flat surface on the internal surface of the swirl chamber.

In a development of the invention, the nozzle comprises a connecting flange in the form of an annular disk, and the periphery of the connecting flange is provided with the at least first flat surface, against which the sonotrode can be placed.

In this way, nozzles equipped with an annular connecting flange can be designed such that the test method of the invention can be carried out rapidly and effectively.

In a development of the invention, the nozzle comprises a connecting flange with a connecting screw thread, wherein the first flat surface is disposed in the region of the connecting screw thread and the connecting screw thread is partially discontinued in the region of the first flat surface.

In this way, an effective transfer of ultrasonic energy to the connecting region can also be ensured in ceramic nozzles having a connecting thread.

In a development of the invention, the nozzle is provided with a heat-reflecting mark.

In this way, the mark can also be detected during the process of thermographic image evaluation so that thermographic evaluation or archiving of the test findings is facilitated considerably.

Additional features and advantages of the invention are revealed in the claims and the following description of preferred embodiments of the invention with reference to the drawings. Individual features of the various embodiments shown can be combined in an arbitrary manner without going beyond the scope of the invention. In the drawings:

DETAILED DESCRIPTION

Figures 1, 2:
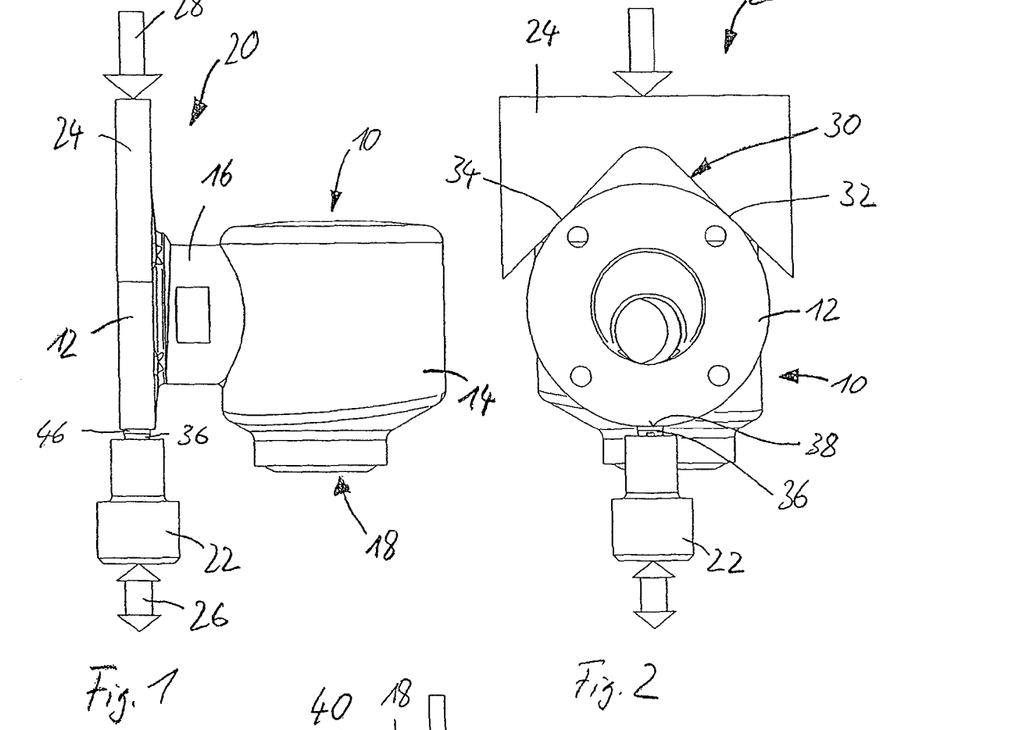
FIG. 1 is a side view of a nozzle of the invention and a testing device of the invention for carrying out the test method of the invention according to a first embodiment.
FIG. 2 is a rear view of the testing device and the nozzle shown in FIG. 1.

The illustration shown in FIG. 1 is a side view of a nozzle 10 composed of ceramic material. The nozzle 10 comprises an annular connecting flange 12, an approximately cylindrical swirl chamber 14, and an inlet tube 16 adapted to interconnect the connecting flange and the swirl chamber 14. The swirl chamber is provided with an outlet orifice 18.

The nozzle 10 is clamped in a testing device 20 shown only partially in the figure. More specifically, the testing device comprises a sonotrode 22 for the transfer of ultrasonic energy and a counterbrace 24. The connecting flange 12 is clamped between the sonotrode 22 and the counterbrace 24. A double arrow 26 signifies the generation of longitudinal vibration by the sonotrode 22. An arrow 28 denotes a counteracting force applied by the counterbrace 24.

The sonotrode 22 is provided with a stamper 36. A disk 46 composed of beechwood is disposed between the stamper 36 and the connecting flange 12. The disk 46 serves as a resilient intermediate component and prevents the periphery of the connecting flange 12 composed of ceramic material from being damaged by the stamper 36. However, the intermediate component causes only an acceptable loss of the transferred sonic power. The beechwood disk 46 has a modulus of elasticity of approximately 14,000 N/mm$^2$ and a thermal conductivity of 0.16 W/mK. Thus the heat inevitably evolved by the transfer of ultrasonic energy by means of the disk 46 can dissipate effectively toward the ambient atmosphere and does not lead to any destruction of the disk 46.

The illustration shown in FIG. 2 is a rear view of the nozzle 10 and the testing device 20, that is to say, a view showing the interior of the inlet of the nozzle 10. The counterbrace 24 comprises an approximately V-shaped cutout 30, in which the annular connecting flange 12 is accommodated. Thus the connecting flange 12 rests at its periphery against the counterbrace 24 at two points of contact 32, 34. The sonotrode 22 rests by way of a stamper 36 against the periphery of the connecting flange 12 with interposition of the resilient disk 46. In the region of a flat surface 38 on the periphery of the connecting flange 12, the stamper 36 of the sonotrode 22 rests against the connecting flange, that is, against the disk 46. Thus there is a flat region of contact between the stamper 36 and the periphery of the connecting flange 12 via the disk 46. Taking the center of the flat region of contact of the stamper 36 as its point of contact between the sonotrode 22 and the connecting flange 12, then it will be seen in FIG. 2 that the two points of contact 32, 34 of the connecting flange 12 on the counterbrace 24 and the point of contact of the stamper 36 of the sonotrode 22 on the flat surface 38 of the connecting flange 12 form a symmetrical planar triangle.

Thus the testing device 20 of the invention is capable of transferring ultrasonic energy to the connecting region of the nozzle 10 in an effective manner. At the same time, the nozzle 10 is capable of vibrating between the points of contact 32, 34 and the stamper 36 such that the ultrasonic energy transferred will be distributed uniformly across the walls of the nozzle 10.

Ultrasonic energy having a frequency of about 20 kHz is transferred to the nozzle 10 by means of the sonotrode 22. Ultrasonic vibration is transferred to the nozzle 10 at a power level of from 150 W to 200 W. By this means, cracks and defects in the walls of the nozzle 10 are caused to heat up to a greater extent than the surrounding material. This heat can be detected by means of, for example, a thermal imaging camera having a sensitivity of 50 mK.

Figure 3:
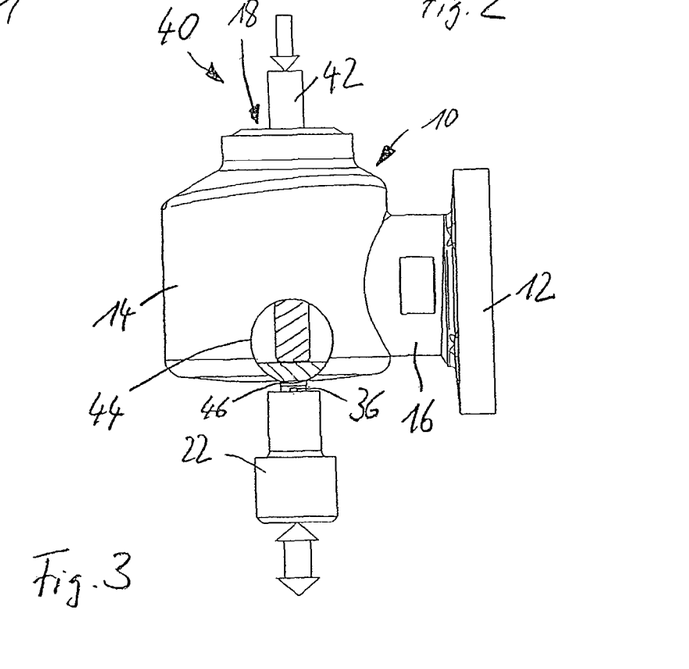
FIG. 3 shows the nozzle shown in FIG. 1 in a testing device of the invention according to a second embodiment.

The illustration shown in FIG. 3 shows the nozzle 10 described with reference to FIG. 1 in a partially illustrated testing device 40 according to a second embodiment of the invention. The testing device 40 comprises a sonotrode 22, which is placed against a flat surface on the top face of the swirl chamber 14, again with interposition of a resilient disk. A rod-shaped counterbrace 42 is inserted through the outlet orifice 18 of the nozzle 10 and rests on an internal surface of the cover of the swirl chamber 14 at a location opposite to the stamper 36 of the sonotrode 22. Here again, a flat surface is provided for the purpose of ensuring a flat region of contact between the counterbrace 42 and the nozzle 10. In order to illustrate the contact of the counterbrace 42 with the internal surface of the swirl chamber 14, a cross-section of the nozzle 10 is shown in a circular region 44 in FIG. 3.

In the testing device shown in FIG. 3, ultrasonic vibration is transferred to the cover of the swirl chamber 14 from outside and can thence propagate across the walls of the nozzle 10. In the case of the testing device shown in FIG. 1, however, the ultrasonic energy is transferred to the connecting flange 12, whence it can propagate to the walls of the nozzle 10. As can be seen in the illustrations of the nozzle 10 shown in FIG. 1 and in FIG. 3, the nozzle 10 has two portions of greater mass, namely the connecting flange 12 and the swirl chamber 14, which are interconnected by the inlet tube 16. The inlet 16 constitutes a very critical component both during operation and during fabrication of the nozzle, since the material of the nozzle is exposed to maximum stresses at this point. When ultrasonic energy is transferred either to the connecting flange 12, as shown in FIG. 1, or to the region of the swirl chamber 14, as shown in FIG. 3, the inlet is freely accessible for carrying out thermographic evaluation thereof. Thus the test method of the invention makes it possible to achieve reliable and thorough examination of ceramic nozzles, more particularly of the critical inlet 16.

Figures 4, 5, 6, 7:
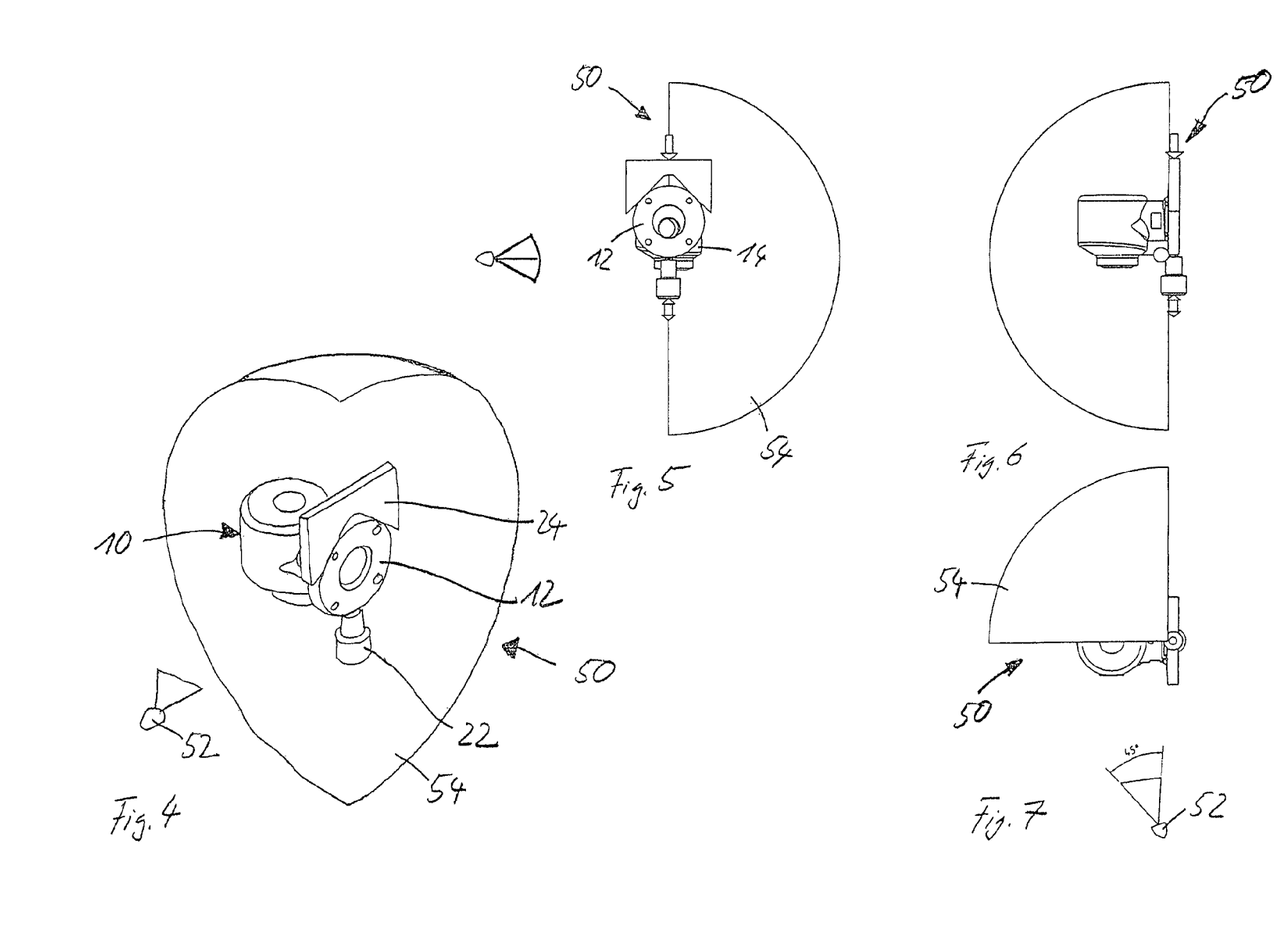
FIG. 4 is an oblique top view of a testing device of the invention according to a third embodiment.
FIG. 5 is a rear view of the testing device shown in FIG. 4.
FIG. 6 is a side view of the testing device shown in FIG. 4.
FIG. 7 is a top view of the testing device shown in FIG. 4.

The illustration shown in FIG. 4 shows a further testing device 50 of the invention with the nozzle 10. As in the case of the testing device 20 shown in FIG. 1, the testing device 50 comprises a sonotrode 22 and a counterbrace 24, between which the connecting flange 12 of the nozzle 10 is clamped. A thermal imaging camera 52—symbolically illustrated—is also provided, of which the field of view is directed toward the nozzle 10. Such a thermal imaging camera is likewise present in the testing devices 20, 40 shown in FIGS. 1 to 3 but is not shown in these figures for the sake of clarity.

The testing device 50 further comprises a heat-reflecting mirror 54 in the form of a spherical shell-segment. The mirror 54 capable of reflecting heat rays extends over a peripheral region of 45°. The viewing direction of the thermal imaging camera 52 is directed toward the mirror 54. Thus the thermal imaging camera 52 can evaluate the front side of the nozzle 10 located at the front in FIG. 4 and also, via the mirror image of the nozzle 10 in the mirror 54, the rear side of the nozzle and its surface located in front in the left half of FIG. 4. Furthermore, the spherical shell-shape of the mirror 54 makes it possible to detect and evaluate the underside and the top face of the nozzle 10 by means of the thermal imaging camera 52.

Thus substantially the entire external surface of the nozzle 10 can be evaluated thermographically without having to move the thermal imaging camera 52 or the mirror 54. In this way, the nozzle 10 can be examined particularly rapidly and thoroughly. The testing device 50 can still be of an economical design, since there is no need to provide any traversing mechanisms for the thermal imaging camera 52, the sonotrode 22, the counterbrace 24, or the mirror 54.

Advantageously, the thermal imaging camera 52 is equipped with a wide-angle lens having a detection range of approximately 45°, so that both the nozzle 10 and the mirror 54 can be recorded in a single image. Wide-angle lenses are further characterized by a greater depth of field so that the mirror 54 can be positioned further away from the thermal imaging camera 52, if appropriate, so as to alleviate any fear of shadows being formed. Thus the thermal imaging camera 52 can capture sharp images of both the nozzle 10 itself and its mirror image in the mirror 54.

The illustration shown in FIG. 5 is a rear view of the testing device 50, that is to say, a view of the interior of the connecting flange 12 toward the swirl chamber 14.

The illustration shown in FIG. 6 is a side view of the testing device 50.

The illustration shown in FIG. 7 is a top view of the testing device 50. The range of detection of 45° of the thermal imaging camera 52 and the reflecting angle of the mirror 54, which is likewise 45°, can be seen in the figure. The range of detection of the thermal imaging camera 52 is in the form of a circular cone in order to make it possible to detect substantially the entire internal surface of the mirror 54; see FIG. 4.

Figure 8:
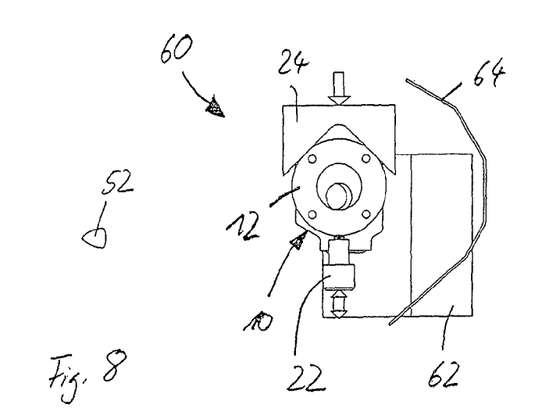
FIG. 8 is a rear view of a testing device of the invention according to a third embodiment.
Figure 9:
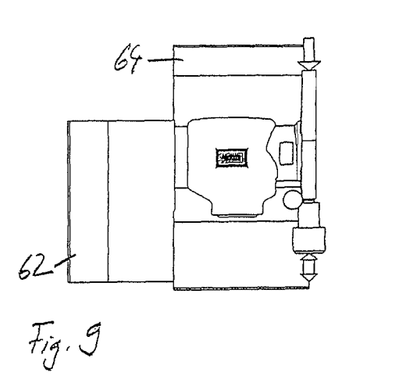
FIG. 9 is a side view of the testing device shown in FIG. 8.

The illustration shown in FIG. 8 is a rear view of a further testing device 60 of the invention, that is to say, a view of the connecting flange 12 of the nozzle 10. The testing device 60 comprises a thermal imaging camera 52, a sonotrode 22, and a counterbrace 24 and it is further provided with two curved mirrors 62, 64. The mirrors 62, 64 are composed of a heat-reflecting material and are in the form of aluminum plates, for example. The mirrors 62, 64 each comprise a plurality of flat surfaces that are inclined in relation to each other.

The mirror 64 is placed in a location opposite to the thermal imaging camera 52 and it therefore makes it possible for the thermal imaging camera 52 to detect not only the front side of the nozzle 10 facing the camera but also the rear side of the nozzle 10 that is remote from the camera. Furthermore, the mirror 64 is curved so as to extend approximately concentrically with the inlet of the nozzle 10 such that the nozzle 10 can also be detected and evaluated from above and below.

Figure 10:
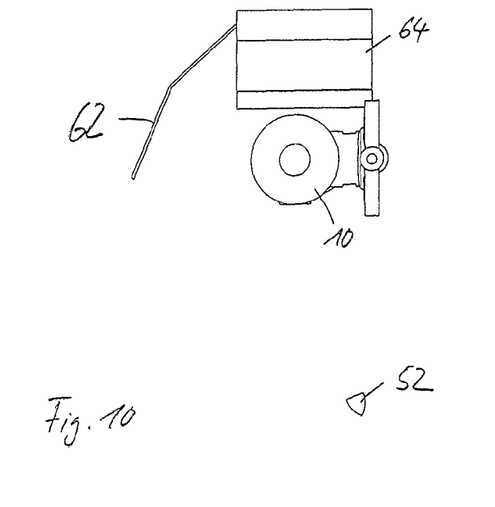
FIG. 10 is a top view of the testing device shown in FIG. 8.

As can be seen from FIG. 10, the mirror 62 is disposed such that the front side of the nozzle 10 can be detected. Thus the mirrors 62, 64 and the thermal imaging camera 52 make it possible to evaluate, thermographically, substantially the entire external surface of the nozzle 10 during the testing procedure except for that side of the connecting flange 12 that is facing the observer in FIG. 8.

Figure 11:
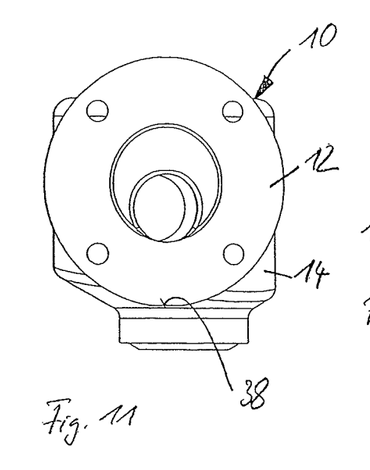
FIG. 11 is a rear view of the nozzle of the invention shown in FIG. 1.

The illustration shown in FIG. 11 is a rear view of the nozzle 10 of the invention, that is to say, a view of the connecting flange 12 directed toward the interior of the swirl chamber 14. The flat surface 38 on the periphery of the otherwise circular connecting flange 12 can be seen in the figure. As mentioned above, this flat surface 38 is provided for accommodation of the stamper 36 of the sonotrode 22; see FIG. 2.

Figure 12:
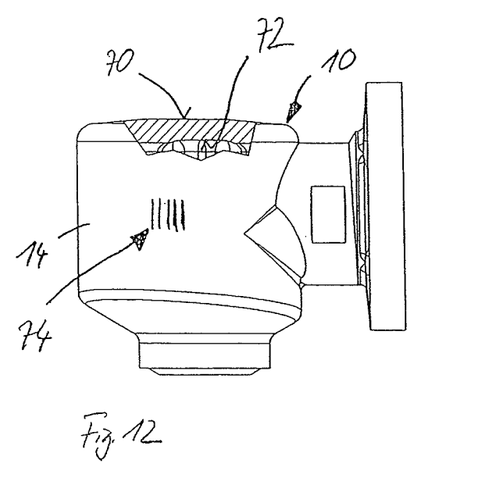
FIG. 12 is a partially cross-sectional side view of the nozzle shown in FIG. 11.

The illustration shown in FIG. 12 is a partially cross-sectional view of the nozzle 10 shown in FIG. 11. On the external surface of the swirl chamber 14 there is disposed a first flat surface 70, and the stamper 36 of the sonotrode 22 can be placed flat against said surface (see FIG. 3) and is subjected to a pressing force. On the opposing internal surface of the swirl chamber 14 there is provided a second flat surface 72, and the counterbrace 42 can then be placed flat against said surface and subjected to a pressing force; see FIG. 3.

Figure 13:
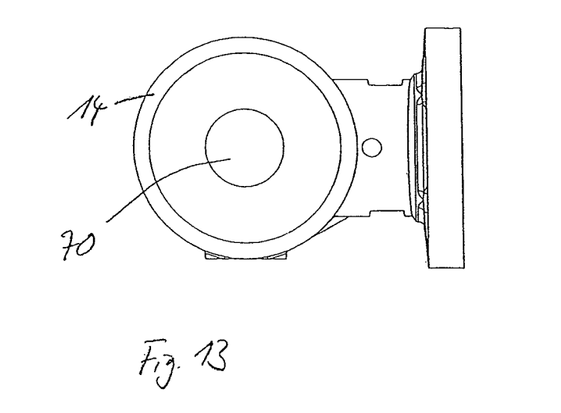
FIG. 13 is a top view of the nozzle shown in FIG. 10.

The illustration shown in FIG. 13 clearly shows the flat surface 70 of a circular shape on the top face of the swirl chamber 14.

In FIG. 12, an external surface of the swirl chamber 14 is provided with a mark 74 in the form of a bar code. This mark 74 is applied in the form of a heat-reflecting coating, for example, by means of silver paint or a soft lead pencil. Thus this mark 74 also appears in the thermal image captured by the camera during thermographic evaluation of the nozzle being tested. This considerably facilitates the evaluation and also the archiving of the test findings.

Figure 14:
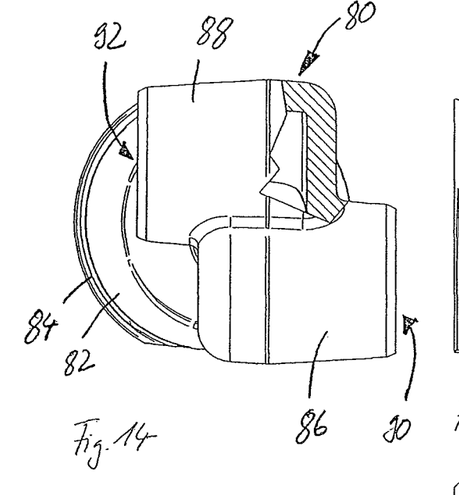
FIG. 14 is a partially cross-sectional front view of a nozzle of the invention according to a further embodiment.
Figure 15:
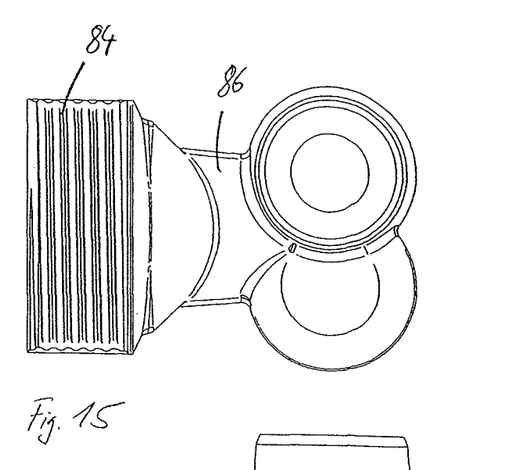
FIG. 15 is a top view of the nozzle shown in FIG. 14.

The illustration shown in FIG. 14 is a partially cross-sectional front view of a nozzle 80 of the invention. The nozzle 80 comprises a connecting flange 82 provided with a male screw thread 84, an approximately tubular inlet 86 (see FIG. 15) and two swirl chambers 86, 88 that are connected to the connecting flange 82 by means of the inlet 86. The swirl chambers 86, 88 are open to the atmosphere in mutually opposing directions by way of outlet orifices 90, 92. The internal and external surfaces of the swirl chamber 88 shown in a partially cross-sectional view each comprise a flat surface for accommodation of a sonotrode or a counterbrace, respectively.

Figure 16:
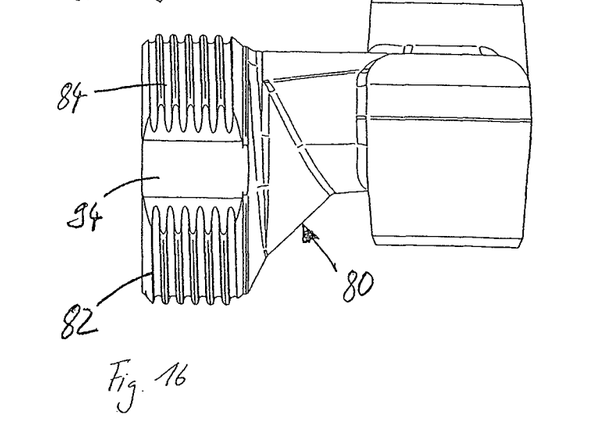
FIG. 16 is a side view of the nozzle shown in FIG. 14.

A flat surface 94 the periphery of the connecting flange 82 can be seen in the side view of the nozzle 80 shown in FIG. 16. The male screw thread 84 is discontinued in the region of this flat surface. The flat surface 94 serves for accommodation of the stamper 36 of the sonotrode 22; see FIG. 1. In this way, effective transfer of ultrasonic energy is also possible when the connecting flange 82 is provided with a male screw thread 84. The flat surface 94 can be rectangular, as shown, or alternatively of circular or oval in shape, for example, and it is dimensioned so as to be slightly larger than the stamper 36.

The invention claimed is:

1. A test method for nozzles comprising the following steps:
    transfer of ultrasonic vibration to said nozzle by means of a sonotrode placed against a connecting region or a chamber region of said nozzle at a point of contact;
    application of a force for pressing said sonotrode against said nozzle during the transfer of ultrasonic vibration;
    use of at least one counterbrace for the purpose of absorbing said pressing force, said counterbrace being placed against only two points of contact on said nozzle, the point of contact of said sonotrode and the two points of contact of said counterbrace forming the corners of a symmetrical planar triangle; and
    thermographic evaluation of the heat evolved in a wall of said nozzle.

2. The test method as defined in claim 1, wherein said sonotrode is placed against said connecting region of said nozzle.

3. The test method as defined in claim 2, wherein said sonotrode is placed against a peripheral surface of said connecting region.

4. The test method as defined in claim 1, wherein said sonotrode is placed against a flat surface in the connecting region or chamber region of said nozzle.

5. The test method as defined in claim 1, wherein said sonotrode is placed against an external or internal surface of a wall in the chamber region of said nozzle.

6. The test method as defined in claim 5, wherein said counterbrace is placed against the internal or external surface of said wall at a location opposite to said sonotrode.

7. The test method as defined in claim 1, wherein a resilient intermediate component is disposed between said sonotrode and said nozzle.

8. The test method as defined in claim 7, wherein said intermediate component has a modulus of elasticity which ranges from 9,000 N/mm$^2$ to 19,000 N/mm$^2$.

9. The test method as defined in claim 8, wherein said intermediate component has a thermal conductivity ranging from 0.1 W/mK to 0.2 W/mK.

10. The test method as defined in claim 8, wherein said modulus of elasticity is 14,000 N/mm$^2$.

11. The test method as defined in claim 1, wherein at least one heat reflecting mirror is disposed in the region of said nozzle and the thermographic evaluation comprises evaluating a mirror image of said nozzle.

12. The test method as defined in claim 11, wherein said heat reflecting mirror is a curved or bent mirror.

13. The test method as defined in claim 11, wherein the test method further comprises movement of said mirror and/or a thermal imaging camera during said thermographic evaluation.

14. The test method as defined in claim 1, wherein the transfer of ultrasonic vibration is at a frequency of about 20 kHz.

15. The test method as defined in claim 1, wherein the transfer of ultrasonic vibration is at a power level which ranges from 100 W to 200 W.

16. The test method as defined in claim 15, wherein said power level is 150 W.

17. The test method as defined in claim 1, further comprising the application of a mark to said nozzle prior to said thermographic evaluation using a heat-reflecting coating material or by means of a heat source.

18. The method of claim 1, wherein the nozzle is of a durable material having a thermal conductivity less than that of metal.

19. The method of claim 18, wherein the material is a ceramic material.

20. A testing device for a nozzle, comprising at least one sonotrode for the purpose of transferring ultrasonic vibration to said nozzle, at least one thermal imaging camera for thermographic evaluation of the heat evolved in a wall of said nozzle, and at least one counterbrace placed against a connection region or a chamber region of the nozzle at a location opposite to said sonotrode, the counterbrace resting against only two points of contact on said nozzle, wherein said two points of contact form, together with a point of contact of said nozzle with said sonotrode, a symmetrical planar triangle.

21. The testing device as defined in claim 20, further comprising heat-reflecting mirrors, wherein a mirror image of said nozzle is evaluated by use of said thermal imaging camera.

22. The testing device as defined in claim 20, further comprising a disk composed of resilient material having a modulus of elasticity ranging from 9,000 N/mm$^2$ to 19,000 N/mm$^2$, disposed between said sonotrode and said nozzle.

23. The testing device as defined in claim 22, wherein said modulus of elasticity is 14,000 N/mm$^2$.

24. A method for testing nozzles, the method comprising the steps of:
    providing a testing device comprising a sonotrode and a counterbrace;
    providing a thermographic measuring device;
    providing a nozzle to be tested for defects, the nozzle being comprised of a material that is durable and has a thermal conductivity less than that of metal, the nozzle having a cavity therein;
    placing the sonotrode in contact with the nozzle and placing the counterbrace against the nozzle at only two points of contact, which two points of contact together with the sonotrode contact with the nozzle form the corners of a symmetrical planar triangle, the counterbrace being spaced apart from the sonotrode;
    energizing the sonotrode such that it provides ultrasonic vibration to the nozzle; and
    using the thermographic measuring device to evaluate the amount of heat evolved from a wall of the nozzle to determine whether the nozzle has a defect.

25. The method of claim 24, wherein the sonotrode is placed against a connecting region or a chamber region of the nozzle.

26. The method of claim 24, wherein the counterbrace is placed against a connecting region or a chamber region of the nozzle.

* * * * *